US012773511B2

(12) United States Patent
Geraghty et al.

(10) Patent No.: US 12,773,511 B2
(45) Date of Patent: Oct. 27, 2026

(54) VENTILATION TUBE INTRODUCER

(71) Applicants: Scott P. Geraghty, Peabody, MA (US); Tyler J. Harrington, Westford, MA (US)

(72) Inventors: Scott P. Geraghty, Peabody, MA (US); Tyler J. Harrington, Westford, MA (US)

( * ) Notice: Subject to any disclaimer, the term of this patent is extended or adjusted under 35 U.S.C. 154(b) by 0 days.

(21) Appl. No.: 18/641,117

(22) Filed: Apr. 19, 2024

(65) Prior Publication Data

US 2025/0325770 A1 Oct. 23, 2025

(51) Int. Cl.
*A61M 16/04* (2006.01)
*A61B 17/34* (2006.01)

(52) U.S. Cl.
CPC ..... *A61M 16/0488* (2013.01); *A61B 17/3415* (2013.01); *A61B 2017/3454* (2013.01)

(58) Field of Classification Search
CPC ........... A61M 16/0488; A61B 17/3415; A61B 2017/3454; A61B 1/267-2736
USPC ..................................................... 128/200.26
See application file for complete search history.

(56) References Cited

U.S. PATENT DOCUMENTS

| | | | | |
|---|---|---|---|---|
| 6,010,520 | A | 1/2000 | Pattison | |
| 2014/0018626 | A1 | 1/2014 | Lee | |
| 2019/0014980 | A1 | 1/2019 | Herskovic | |
| 2019/0388635 | A1 * | 12/2019 | Loewen | A61B 1/06 |
| 2022/0152329 | A1 * | 5/2022 | Lucchina | A61B 1/00151 |

FOREIGN PATENT DOCUMENTS

| | | | | |
|---|---|---|---|---|
| EP | 2875841 | A1 | 5/2015 | |
| GB | 2504581 | A * | 2/2014 | A61M 16/0488 |
| GB | 2507474 | A * | 5/2014 | A61M 16/0488 |
| WO | 2020/182851 | A1 | 9/2020 | |

OTHER PUBLICATIONS

No Mentioned Authors, VBM Intubation Aids Stylets / Introducers / Tube exchanger, Retrieved Jun. 7, 2024 from https://media.vbm-medical.de/fly/FLY013_EN.pdf, link found on https://www.vbm-medical.de/en/products/airway-management/intubation-aids/s-guide/, No Publication Date Mentioned.

No Mentioned Authors, VBM Soft and autraumatic tip Oxygenation* Malleability, Retrieved Jun. 7, 2024 from https://media.vbm-medical.de/pro/PRO019_EN.pdf, link found on https://www.vbm-medical.de/en/products/airway-management/intubation-aids/s-guide/, No Publication Date Mentioned.

* cited by examiner

*Primary Examiner* — Kendra D Carter
*Assistant Examiner* — Arielle Wolff
(74) *Attorney, Agent, or Firm* — Secant IP, PLLC; Michael J. Gallagher

(57) ABSTRACT

A medical device, comprising a ventilation tube introducer; the ventilation tube introducer in a form of a plastic shaft having a longitudinal axis; the plastic shaft having two shaft members arranged axially along the longitudinal axis; the two shaft members provided by a shaft proximal member and a shaft distal member; a proximal terminal end of the introducer provided by the shaft proximal member and a distal terminal end of the introducer provided by the shaft distal member; the shaft proximal member and the shaft distal member are joined to each other; and the shaft proximal member formed of plastic and the shaft distal member formed of an elastomer having a hardness which is lower than a hardness of the plastic of the shaft proximal member.

27 Claims, 4 Drawing Sheets

VENTILATION TUBE INTRODUCER

FIELD

The present disclosure relates to medical devices, and more particularly a ventilation tube introducer, and even more particularly an endotracheal tube introducer.

BACKGROUND

Proper placement of an endotracheal tube in the airway of an individual during intubation (translaryngeal insertion) may be difficult to perform on certain individuals due to their anatomy. In order to provide a guide for the endotracheal tube prior to insertion, an endotracheal tube introducer may be inserted in the airway prior to insertion of the endotracheal tube. Once the endotracheal tube introducer reaches its destination, the ventilation passageway of the endotracheal tube is disposed coaxially over the endotracheal tube introducer, and the endotracheal tube is then inserted into the airway by sliding along the endotracheal tube introducer.

Endotracheal tube introducers are known to be formed of a single-piece (monolithic) plastic shaft with a blunt tip. The blunt tip is meant to be atraumatic, however, the blunt tip may still cause tissue damage during insertion due to the rigidity of the plastic shaft.

SUMMARY

The present disclosure provides a ventilation tube introducer, and even more particularly an endotracheal tube introducer, with a soft atraumatic tip to reduce the possibility of tissue damage during insertion of the introducer in the airway of a patient/host.

In certain embodiments, a medical device is provided, comprising a ventilation tube introducer; the ventilation tube introducer in a form of a plastic shaft having a longitudinal axis; the plastic shaft having two shaft members arranged axially along the longitudinal axis; the two shaft members provided by a shaft proximal member and a shaft distal member; a proximal terminal end of the introducer provided by the shaft proximal member and a distal terminal end of the introducer provided by the shaft distal member; the shaft proximal member and the shaft distal member are joined to each other; and the shaft proximal member formed of plastic and the shaft distal member formed of an elastomer having a hardness which is lower than a hardness of the plastic of the shaft proximal member.

In certain embodiments, the shaft distal member has a bulbous tip which forms the terminal end of the introducer.

In certain embodiments, the shaft distal member is conical proximally adjacent the bulbous tip and distally adjacent the shaft proximal member.

In certain embodiments, the bulbous tip is spherical and has a diameter in a range of 2 mm to 5 mm.

In certain embodiments, the shaft proximal member has a distal end region having an outer diameter; the shaft distal member has a proximal end region having an outer diameter; and the outer diameter of the distal end region of the shaft proximal member and the outer diameter of the proximal end region of the shaft distal member are substantially equal.

In certain embodiments, the shaft has a shaft proximal segment and a shaft distal segment; the shaft proximal segment extends parallel with the longitudinal axis; and the shaft distal segment extends at an angle relative to the longitudinal axis in a range of 140 degrees to 170 degrees.

In certain embodiments, the shaft distal segment is formed by the shaft proximal member and the shaft distal member.

In certain embodiments, the shaft distal segment is formed only by the shaft distal member.

In certain embodiments, the plastic has a Shore D durometer hardness, as measured by ASTM D2240-15 (2021), in a range of 55 to 70 Shore D durometer hardness; and the elastomer has a Shore A durometer hardness, as measured by ASTM D2240-15 (2021), in a range of 20-80 Shore A durometer hardness.

In certain embodiments, the elastomer has a Shore A durometer hardness, as measured by ASTM D2240-15 (2021), in a range of 25-70 Shore A durometer hardness.

In certain embodiments, the plastic of the shaft proximal member is polyethylene.

In certain embodiments, the plastic shaft has a longitudinal length in a range of 50 to 73 centimeters; and the plastic shaft has an outer diameter in a range of 3 to 6 millimeters.

In certain embodiments, the elastomer of the shaft distal member is polyvinylchoride, polyurethane or polysiloxane.

In certain embodiments, the shaft proximal member and the shaft distal member are at least one of bonded, friction fit, or positively mechanically engaged to each other.

In certain embodiments, the shaft distal member includes a dowel; the shaft proximal member includes a dowel receptacle; and the dowel is disposed in the dowel receptacle.

In certain embodiments, the dowel of the shaft distal member and the dowel receptacle of the shaft proximal member are at least one of bonded, friction fit, or positively mechanically engaged to each other.

In certain embodiments, the dowel receptacle of the shaft proximal member includes a plurality of ridges to grip the shaft distal member and/or a plurality of recesses to grip the shaft distal member.

In certain embodiments, the dowel receptacle of the shaft proximal member is provided by a lumen of the shaft proximal member.

In certain embodiments, the shaft proximal member and the shaft distal member have different colors.

A plurality of ventilation tube introducers, comprising a first ventilation tube introducer and a second ventilation tube introducer of the plurality of ventilation tube introducers; wherein the first ventilation tube introducer is in a form of a plastic shaft having a shaft proximal member and a shaft distal member, wherein the shaft proximal member is formed of plastic and the shaft distal member formed of an elastomer having a hardness which is lower than a hardness of the plastic of the shaft proximal member; wherein the second ventilation tube introducer is in a form of a plastic shaft having a shaft proximal member and a shaft distal member, wherein the shaft proximal member is formed of plastic and the shaft distal member formed of an elastomer having a hardness which is lower than a hardness of the plastic of the shaft proximal member; wherein the shaft distal member of the first ventilation tube introducer has a hardness which is different than the hardness of the shaft distal member of the second ventilation tube, and a color which is different than a color of the shaft distal member of the second ventilation tube which corresponds to the difference in hardness.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein.

DETAILED DESCRIPTION

Figure 1:
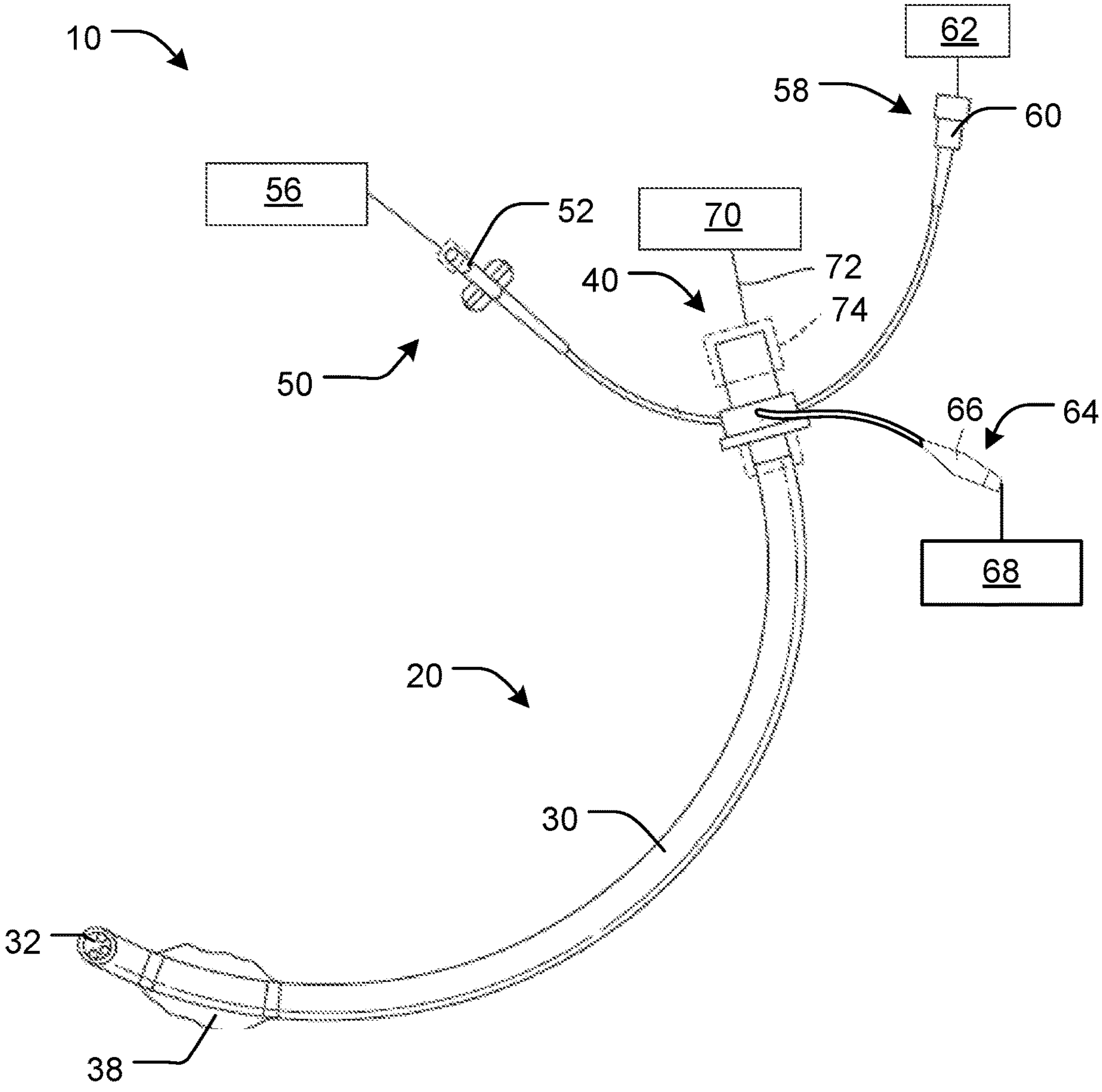
FIG. 1 is a side-view of certain medical devices according to the present disclosure.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

Referring now to the figures, FIG. 1 shows a medical device 10 according to the present disclosure. Medical device 10 comprises an ventilation (breathing) apparatus 20, and more particularly an endotracheal tube apparatus. While the disclosure may refer to the ventilation apparatus 20 as being an endotracheal tube apparatus, particularly for single-use (disposable) applications, it should be understood that the present disclosure is not limited to an endotracheal tube apparatus. Notably, for oral intubation, the ventilation apparatus 20 may otherwise be a supraglottic airway apparatus, such as a supraglottic airway laryngopharyngeal tube (SALT) apparatus, a laryngeal mask airways (LMA) apparatus or a laryngeal tube. Otherwise, for tracheal intubation, the ventilation apparatus 20 may be a cricothyrotomy tube apparatus or a tracheostomy tube apparatus.

As shown, endotracheal tube apparatus 20 comprises a ventilation (breathing) tube 30, and more particularly an endotracheal tube, with a ventilation passageway 32 disposed therein along the length thereof. Endotracheal tube apparatus 20 further comprises a hub connection fitting 40 disposed proximally adjacent to the ventilation tube 30, which is permanently coupled to the ventilation tube 30 and through which the ventilation passageway 32 extends. Among other things, the hub connection fitting 40 operatively connects the ventilation tube 30 to ventilation apparatus 70, which also may be referred to as a ventilator or a respirator. More particularly, a proximal connector portion of the hub connection fitting 40 is dimensioned to be inserted into a passageway 72 of a ventilator tube 74 and removably fit with the inside diameter of the side wall thereof. Ventilation passageway 32 is in fluid communication with ventilator apparatus 70, such as a bag valve mask or a mechanical ventilator as known in the art connected to endotracheal tube apparatus 20, to provide mechanical ventilation/respiration to the patient/host.

In addition, endotracheal tube apparatus 20 comprises a fluid sampling port 50 which is in fluid communication with the ventilation passageway 32 and which has a fluid sampling port connector 52 which connects fluid sampling port 50 to an analyzing/monitoring apparatus 56. More particularly, fluid sampling port 50 may be a carbon dioxide sampling port, and analyzing/monitoring apparatus 56 may be a carbon dioxide analyzer/monitor (e.g. a capnograph).

Furthermore, endotracheal tube apparatus 20 further comprises a drug delivery port 58 which is in fluid communication with the ventilation passageway 32 and which has a drug delivery port connector 60 which connects drug delivery port 58 to a drug delivery device 62, such as a syringe.

Moreover, endotracheal tube apparatus 20 also further comprises a cuff inflation port 64 which is in fluid communication with a inflation cuff 38 and which has a cuff inflation port connector 66 which connects cuff inflation port 64 to a cuff inflation device 68.

Figure 2:
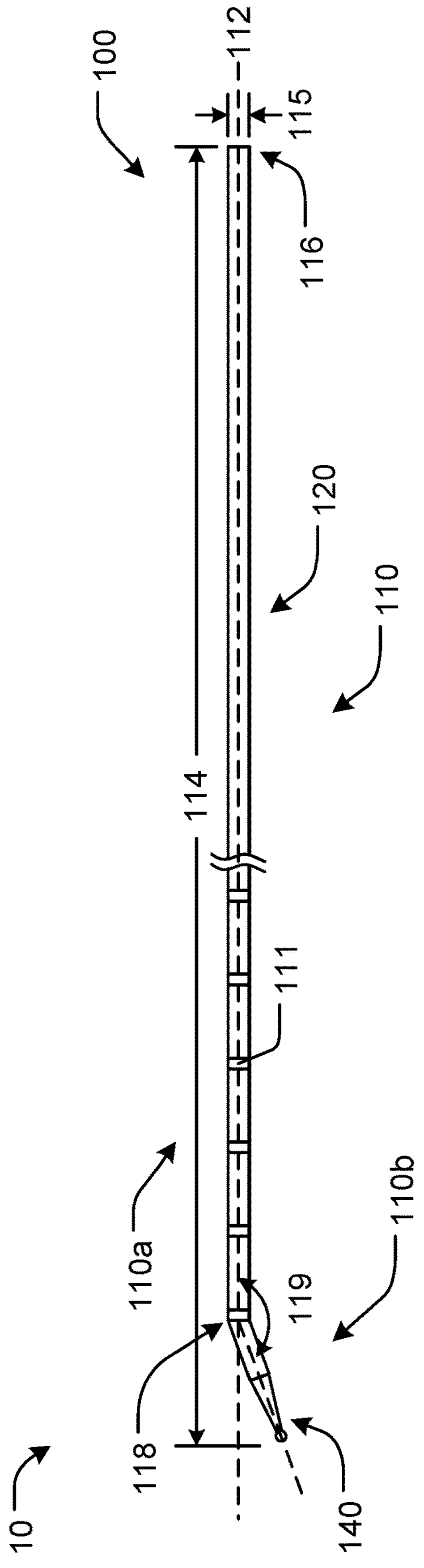
FIG. 2 is a side-view of a ventilation (airway) tube introducer according to the present disclosure, used in conjunction with the medical devices of FIG. 1.

Referring now to FIG. 2, medical device 10 further comprises a single-use (disposable) ventilation (airway) tube introducer 100, and more particularly an endotracheal tube introducer, which may also be referred to as an intubation bougie. As shown, introducer 100 comprises, and more particularly essentially consists of, or consists of, an elongated, cylindrical, plastic shaft 110 formed of two plastic members 120, 140 arranged axially along a longitudinal axis 112. More particularly, plastic shaft 110 comprises a shaft proximal (elongated) member 120, which provides a proximal (terminal) end 116 of the shaft 110/introducer 100, and a shaft distal (elongated) member 140, which provides a distal (terminal) end 117 of the shaft 110/introducer 100.

The shaft proximal member 120 has a longitudinal length in a range of 48 to 72 centimeters (cm), and a uniform outer diameter in a range of 3 to 6 millimeters (mm). The shaft proximal member 120 may include a plurality of different colored bands or other indicia 111 at fixed intervals along its length to indicate depth of insertion to the patient/host.

The shaft proximal member 120 is formed of a single (unitary monolithic) piece of extruded plastic, particularly a thermoplastic, more particularly a polyolefin and even more particularly polyethylene (PE). Moreover, the shaft proximal member 120 is formed of high-density polyethylene (HDPE). The extruded plastic composition may be a plastic composition which has a three-point bending flexural modulus, as measured by ASTM D790-17 (2017) at room temperature (e.g. 23° C.), in a range of 70,000 to 275,000 psi., and more particularly 100,000 to 225,000 psi. Additionally, or alternatively, the plastic composition may have a Shore D durometer hardness, as measured by ASTM D2240-15 (2021) at room temperature (e.g. 23° C.), in a range of 55 to 70 Shore D durometer hardness.

The shaft distal member 140 has a longitudinal length in a range of 1 to 3 centimeters (cm). The shaft distal member 140 is formed of a single (unitary monolithic) piece of (injection) molded thermoplastic, particularly an elastomer, which may be either a thermoplastic elastomer or a thermoset elastomer. More particularly, the elastomer may be formed of polyvinylchoride, polyurethane or polysiloxane (commonly referred to as silicone). The plastic composition may have a Shore A durometer hardness, as measured by ASTM D2240-15 (2021) at room temperature (e.g. 23° C.), in a range of 20-80 Shore A durometer hardness and more particularly 25-70 Shore A durometer hardness as measured by ASTM D2240-15 (2021).

The elastomer composition may be composition with a glass transition temperature (Tg) below 23° C. and which is at most, 50% crystalline (i.e., the composition contains an amorphous phase of 50% or greater, up to 100% amorphous phase). Additionally, or alternatively, the elastomer composition may be a composition that has an elongation at 23° C. of at least 100%, and which, after being stretched to twice its original length and being held at such for one minute, may recover in a range of 50% to 100% within one minute after release from the stress. More particularly, the elastomer composition may recover in a range of 75% to 100% within one minute after release from the stress, and even more particularly recover in a range of 90% to 100% within one minute after release from the stress.

In certain embodiments, the shaft distal member 140 of different introducers 100 may be color coded to the hardness of the shaft distal member 140. In other words, a first color (e.g. green) of the shaft distal member 140 may be matched/correspond to a first hardness (e.g. 25-40 Shore A) of the shaft distal member 140; a second color (e.g. blue) of the shaft distal member 140 may be matched/correspond to a greater (second) hardness (e.g. 41-59 Shore A) of the shaft distal member 140; a third color (e.g. violet) of the shaft distal member 140 may be matched/correspond to an even greater (third) hardness (e.g. 60-80 shore A) of the shaft distal member 140. In the foregoing manner, a clinician or other medical treatment personnel may be quickly made aware of the hardness of the shaft distal member 140 for selection. Introducers 100 having a different (Shore A) durometer hardness may be packaged or otherwise provided as part of a kit, or packaged individually and listed in a product (inventory) offering from a same source.

In certain embodiments, the shaft proximal member 120 of different introducers 100 may be color coded to the size of the introducer 100. In other words, a first color (e.g. red) of the shaft proximal member 120 may be matched/correspond to a first size (e.g. small such as 6 French) of the introducer 100; a second color (e.g. orange) of the shaft proximal member 120 may be matched/correspond to a second size (e.g. medium/intermediate such as 10 French) of the introducer 100; a third color (e.g. yellow) of the shaft proximal member 120 may be matched/correspond to a third size (e.g. large such as 15 French) of the introducer 100. In the foregoing manner, a clinician or other medical treatment personnel may be quickly made aware of the size of the introducer 100 for selection. Introducers 100 having a different (e.g. French) size may be packaged or otherwise provided as part of a kit, or packaged individually and listed in a product (inventory) offering from a same source.

Also, in certain embodiments, the first hardness (e.g. 25-40 Shore A) of the shaft distal member 140 may be coupled with the first size (e.g. small such as 6 French) of the introducer 100; the second hardness (e.g. 41-59 Shore A) of the shaft distal member 140 may be coupled with the second size (e.g. medium/intermediate such as 10 French) of the introducer 100; and the third hardness (e.g. 60-80 Shore A) of the shaft distal member 140 may be coupled with the third size (e.g. large such as 15 French) of the introducer 100. In other words, as the size of the introducer 100 increases, the hardness of the shaft distal member 140 increases, or alternatively, as the size of the introducer 100 decreases, the hardness of the shaft distal member 140 decreases. In such manner, the smallest introducer 100 will have the softest shaft distal member 140, which may be most suitable for pediatric use. In the foregoing manner, a clinician or other medical treatment personnel may be quickly made aware of the hardness of the shaft distal member 140 and size of the introducer 100 for selection. Introducers 100 having a different (Shore A) durometer hardness and size may be packaged or otherwise provided as part of a kit, or packaged individually and listed in a product (inventory) offering from a same source.

Also, the difference in color between the shaft proximal member 120 and the shaft distal member 140 may be used by a clinician or other medical personnel to indicate proper positioning of the distal member 140 through the vocal cords and the airway, as opposed to the improper positioning in the esophagus.

As shown, both the shaft proximal member 120 and the shaft distal member 140 may have a solid cross-section along their respective lengths (i.e. no internal lumen or other passageway). Moreover, the introducer 100 may be understood as being non-steerable (i.e. does not having a steering mechanism within the shaft proximal member 120 or the shaft distal member 140). The introducer 100 has an overall longitudinal length 114 in a range of 50 to 75 centimeters (cm) and an outer diameter 115 in a range of 3 to 6 millimeters (mm).

Figure 8:
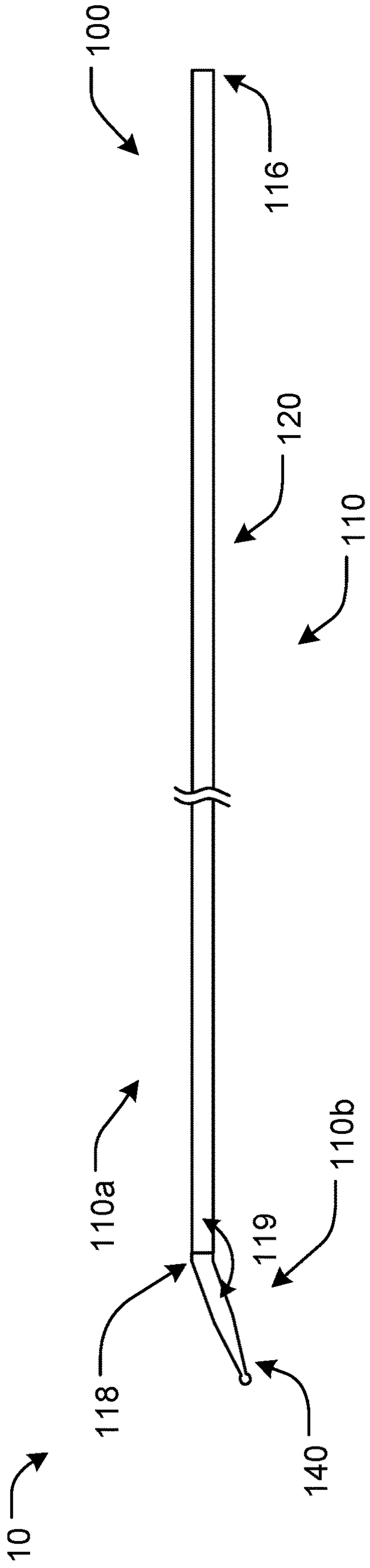
FIG. 8 is a side-view of a ventilation (airway) tube introducer according to another embodiment of the present disclosure.

As shown, a distal end segment **110*b* of the shaft 110 extends along the longitudinal axis 112 from a bend 118 formed at an obtuse angle 119 relative to a proximal end segment 110*a* of the shaft 110, which extends parallel with the longitudinal axis 112. As shown, the distal end segment 110*b* is formed by both the shaft proximal member 120 and the shaft distal member 140, and the angle 119 is in a range of 135 degrees to 165 degrees relative to the longitudinal axis 112, and more particularly 150 degrees (e.g. to facilitate passage anteriorly under the epiglottis and through the vocal cords). In other embodiments, as shown in FIG. 8, the distal end segment 110*b* is formed only by the shaft distal member 140**. The shaft distal segment has a longitudinal length of 2 to 4 cm.

The shaft distal member 140 has a proximal end region 144, which has a proximal end face 146. Proximal end region 144/proximal end face 146 has an outer diameter which is substantially equal (e.g. within 0.05 mm of being equal) to an outer diameter of a distal end region 124/distal end face 126 of the shaft proximal member 120.

Figure 3:
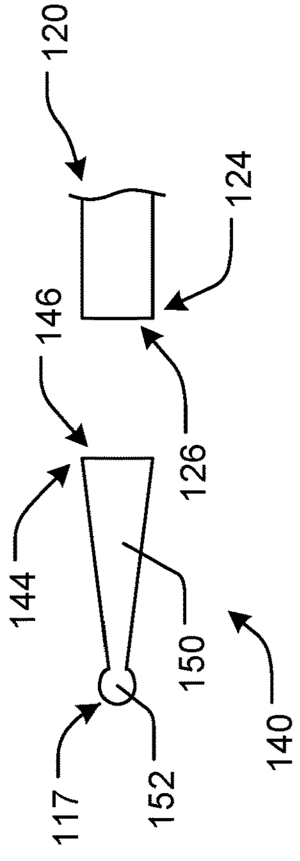
FIG. 3 is a close-up side-view of a shaft proximal member and a shaft distal member of the introducer of FIG. 2, prior to assembly.

As shown in FIG. 3, the distal end face 126 of the shaft proximal member 120 and the proximal end face 146 of the shaft distal member 140 are completely planar and circular. The two end faces 126, 146 may then be placed in contact adjacent one another and joined (abutting) to each other with a butt-joint.

Joining may be accomplished by first treating the distal end face 126 of the shaft proximal member 120 with a corona, plasma, flame or other treatment to raise the surface energy of the plastic (polyethylene). Once treated, the distal end face 126 of the shaft proximal member 120 and/or the proximal end face 146 of the shaft distal member 140 may be heated above room temperature (e.g. 27° C.) to a suitable temperature until face 126 and/or face 146 has softened and/or melted, such as by a hot plate, and then pressed directly together under pressure until cooled to provide a (cohesive or adhesive) bond, without use of a separate adhesive (i.e. adhesiveless).

Alternatively, the distal end face 126 of the shaft proximal member 120 and the proximal end face 146 of the shaft distal member 140 may be directly welded (e.g. hot air welded, ultrasonic) to each other to provide a (cohesive or adhesive) bond, without use of a separate adhesive (i.e. adhesiveless).

In other embodiments, the shaft distal member 140 may be molded-in-place directly to the shaft proximal member 120, such as by insert (injection) molding, to provide a (cohesive or adhesive) bond, without use of a separate adhesive (i.e. adhesiveless).

In still other embodiments, a separate adhesive, such as a reactive (e.g. cyanoacrylate, epoxy) adhesive may be applied to the distal end face 126 of the shaft proximal member 120 and/or the proximal end face 146 of the shaft distal member 140 and the two faces 126, 146 may be pressed together with pressure until the adhesive sets and a (cohesive or adhesive) bond is formed.

Figure 4:
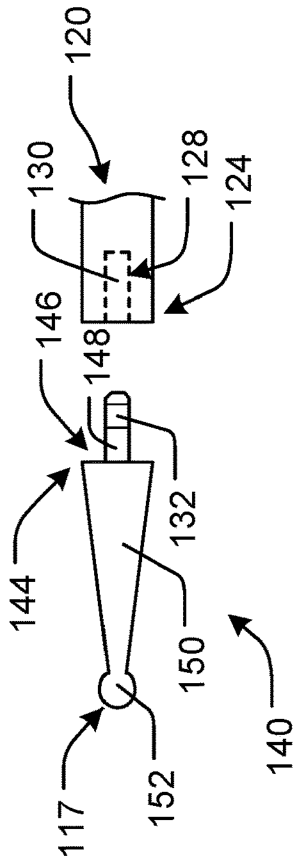
FIG. 4 is a close-up side-view of another embodiment of the shaft proximal member and the shaft distal member of the introducer of FIG. 2, prior to assembly.

In another embodiment, as shown in FIG. 4, the distal end face 126 of the distal end region 124 of the shaft proximal member 120 may include a centrally disposed cylindrical dowel receptacle 128, shown as a blind hole 130, while the proximal end face 146 of the proximal end region 144 of the shaft distal member 140 includes a centrally disposed cylindrical dowel 148. The shaft proximal member 120 and the shaft distal member 140 may be assembled by inserting and disposing the dowel 148 within the dowel receptacle 128 to form a dowel joint.

The dowel 148 and the dowel receptacle 128 are particularly arranged such that the dowel 148 is disposed on the shaft distal member 140, and the dowel receptacle 128 is disposed on the shaft proximal member 120. In a vice-versa arrangement, the dowel 148, if on the shaft proximal member 120, being inserted into the dowel receptacle 128, if on the shaft distal member 140, may be understood to make the shaft distal member 140 too rigid.

In certain embodiments, due to the flexibility of the composition used for the shaft distal member 140, the dowel 148 may be held or otherwise retained in the dowel receptacle 128 via a friction fit connection (which also may be referred to as an interference fit, press fit or pressure grip). A friction fit connection may be understood as a connection formed between the components which relies upon friction to inhibit separation of the components, particularly by one of the components being pressed into the other component such that at least one of the components is compressed (deformed) against the another.

In other embodiments, the dowel 148 may be held or otherwise retained in the dowel receptacle 128 by an adhesive (coating) 132 disposed in on the dowel 148 an/or the dowel receptacle 128 prior to inserting the dowel 148 within the dowel receptacle 128.

Figure 5:
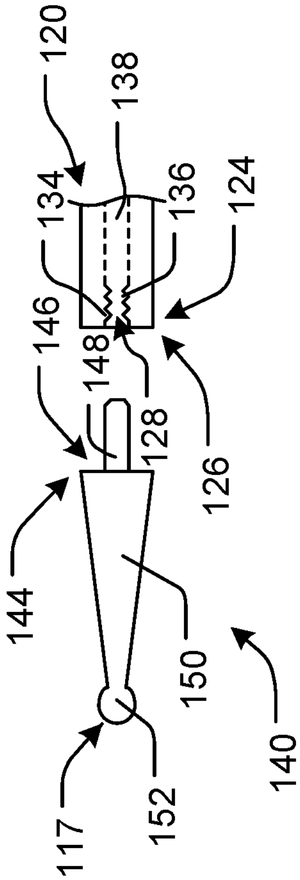
FIG. 5 is a close-up side-view of another embodiment of the shaft proximal member and the shaft distal member of the introducer of FIG. 2, prior to assembly.

In still another embodiments, the dowel 148 may be held or otherwise retained in the dowel receptacle 128 via a (positive) mechanical engagement connection. A (positive) mechanical engagement may be understood herein as a connection formed between the components which does not rely solely on friction to inhibit separation of the components and which includes a mechanical interlock to inhibit separation of the components (e.g. overlapping surfaces). As shown in FIG. 5, the dowel receptacle 128 may include a plurality of alternating gripping ridges (e.g. projections) 134 and/or gripping recesses (e.g. undercuts) 136 arranged in series along a length of the dowel receptacle 128 to further secure the shaft distal member 140 to the shaft proximal member 120, particularly via the ridges 134 of the shaft proximal member 120 penetrating into the softer shaft distal member 140 and the shaft distal member 140 occupying the recesses 136 of the shaft proximal member 120. It should be understood that (positive) mechanical engagement may include threaded (e.g. screw) engagement.

Figure 6:
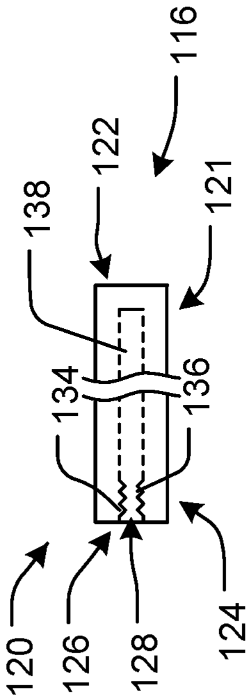
FIG. 6 is a close-up side-view of another embodiment of the shaft proximal member of the introducer of FIG. 2.

Also, the blind hole 130 previously forming the dowel receptacle 128 may be replaced with a bore 138 which extends along substantially a whole length of the shaft proximal member 120, which may be formed as a lumen when the shaft proximal member 120 is extruded hollow. The bore 138 may extend all the way through the shaft proximal member 120 during extrusion and then be subsequently sealed, as shown in FIG. 6, at the proximal end region 121 of the shaft proximal member 120 after extrusion, such as by contacting/pressing the proximal end face 122 of the heated extrudate against a forming plate or other tooling, or reheating the shaft proximal member 120 after it has cooled and pressing the bore closed.

Figure 7:
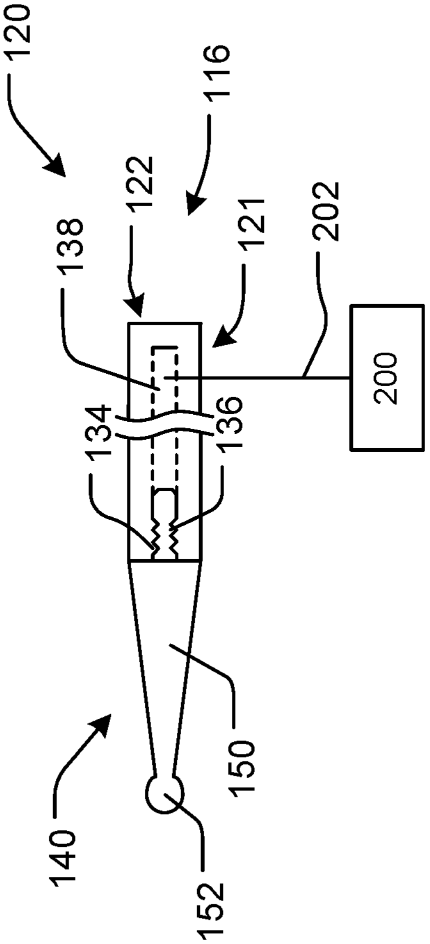
FIG. 7 is a close-up side-view of a ventilation (airway) tube introducer according to another embodiment of the present disclosure.

In still another embodiments, after the shaft proximal member 120 and the shaft distal member 140 are joined as shown in FIG. 7, a vacuum (negative pressure) may be created in the bore 138 with a vacuum generating device 200, particularly to further the strength of the joint against separation. The small diameter heated hollow needle 202 may be used to pierce the wall of the shaft proximal member 120 and enter bore 138, which is coupled to the vacuum generating device 200 to generate a vacuum in the bore 138. As the heated needle 202 is withdrawn, the plastic material forming the wall of the shaft proximal member 120 may flow as to close and seal the hole during withdrawal of the needle 202.

In light of the foregoing, it should be understood that, for patient safety, the shaft proximal member 120 and the shaft distal member 140 are to be permanently joined together, i.e. joined in such a manner as not to be separable, particularly without damage to at least one of the shaft proximal member 120 and the shaft distal member 140, during ordinary use of the introducer 100 for its intended purpose.

Returning to FIG. 3, the shaft distal member 140 continuously tapers distally in a manner of a conical (concentric cone) region 150 to a bulbous (spherical) tip region 152. The conical region 150 at the proximal end region 144/proximal end face 146 has an outer diameter in a range of 3 to 6 millimeters, which tapers to an outer diameter of 1 to 4 mm adjacent the bulbous (spherical) tip region 152, over a length of 5 to 25 mm, and more particularly 7 to 20 mm. The bulbous (spherical) tip region 152 has an outer spherical diameter in a range of 2 to 5 mm which forms the distal terminal end 117 of the introducer 100. In the foregoing manner, the shaft distal member 140 made with the foregoing durometer and structure provides an soft, atraumatic blunt tip to reduce the possibility of tissue damage during insertion of the introducer 100 into the airway of a patient/host.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

LISTING OF REFERENCE CHARACTERS

10 medical device
20 ventilation (breathing) apparatus

30 ventilation (breathing) tube
32 ventilation passageway
38 inflation cuff
40 hub connection fitting
50 fluid sampling port
52 fluid sampling port connector
56 analyzing/monitoring apparatus
58 drug delivery port
60 drug delivery port connector
62 drug delivery device
64 cuff inflation port
66 cuff inflation port connector
68 cuff inflation device
70 ventilator apparatus
72 passageway
74 tube
100 ventilation (airway) tube introducer
110 plastic shaft
110*a* proximal end segment
110*b* distal end segment
111 color bands
112 longitudinal axis
114 longitudinal length
115 outer diameter
116 proximal (terminal) end
117 distal (terminal) end
118 bend
119 angle
120 shaft proximal member
121 shaft proximal member proximal end region
122 shaft proximal member proximal end face
124 shaft proximal member distal end region
126 shaft proximal member distal end face
128 cylindrical dowel receptacle
130 blind hole
132 adhesive
134 gripping ridges
136 gripping recesses
138 bore
140 shaft distal member
144 shaft distal member proximal end region
146 shaft distal member proximal end face
148 cylindrical dowel
150 conical region
152 bulbous (spherical) tip region
200 vacuum generating device
202 needle

What is claimed is:

1. A medical device, comprising:
a non-steerable ventilation tube introducer;
the ventilation tube introducer having a shaft having a longitudinal axis;
the shaft having two shaft members provided by a shaft proximal member and a shaft distal member;
a proximal terminal end of the introducer provided by the shaft proximal member and a distal terminal end of the introducer provided by the shaft distal member;
the shaft proximal member and the shaft distal member are joined to each other;
the shaft proximal member formed of plastic and the shaft distal member formed of an elastomer having a hardness which is lower than a hardness of the plastic of the shaft proximal member;
the shaft distal member is without an internal passageway;
the shaft distal member includes a dowel;
the shaft proximal member includes a dowel receptacle;
the dowel is disposed in the dowel receptacle;
wherein the shaft distal member has a bulbous tip which forms the distal terminal end of the introducer;
the shaft distal member is a single piece having a conical surface which continuously tapers from distally adjacent the shaft proximal member to proximally adjacent the bulbous tip; and
wherein the single piece is a single molding of a single composition.

2. The medical device of claim 1, wherein:
the conical surface is provided by a conical region which has an outer diameter adjacent the shaft proximal member in a range of 3 mm to 6 mm, and an outer diameter adjacent the bulbous tip of 1 mm to 4 mm; and
the conical region has a length of 5 mm to 25 mm.

3. The medical device of claim 1, wherein:
the bulbous tip is spherical and has a diameter in a range of 2 mm to 5 mm.

4. The medical device of claim 1, wherein:
the shaft proximal member has a distal end region having an outer diameter;
the shaft distal member has a proximal end region having an outer diameter; and
the outer diameter of the distal end region of the shaft proximal member and the outer diameter of the proximal end region of the shaft distal member are substantially equal.

5. The medical device of claim 1, wherein:
the shaft has a shaft proximal segment and a shaft distal segment;
the shaft proximal segment arranged along the longitudinal axis;
the shaft distal segment arranged at an angle relative to the longitudinal axis; and
the angle is in a range of 140 degrees to 170 degrees.

6. The medical device of claim 5, wherein:
the shaft distal segment is formed by the shaft proximal member and the shaft distal member.

7. The medical device of claim 5, wherein:
the shaft distal segment is formed only by the shaft distal member.

8. The medical device of claim 1, wherein:
the plastic has a Shore D durometer hardness, as measured by ASTM D2240-15 (2021), in a range of 55 to 70 Shore D durometer hardness; and
the elastomer has a Shore A durometer hardness, as measured by ASTM D2240-15 (2021), in a range of 20-80 Shore A durometer hardness.

9. The medical device of claim 8, wherein:
the elastomer has a Shore A durometer hardness, as measured by ASTM D2240-15 (2021), in a range of 25-70 Shore A durometer hardness.

10. The medical device of claim 1, wherein:
the plastic of the shaft proximal member is polyethylene.

11. The medical device of claim 1, wherein:
the shaft proximal member has a longitudinal length in a range of 48 to 72 centimeters; and
the shaft proximal member has an outer diameter in a range of 3 to 6 millimeters.

12. The medical device of claim 1, wherein:
the elastomer of the shaft distal member is polyvinylchoride, polyurethane or polysiloxane.

13. The medical device of claim 1, wherein:
the shaft proximal member and the shaft distal member are bonded to each other.

14. The medical device of claim 1, wherein:
the dowel of the shaft distal member and the dowel receptacle of the shaft proximal member are bonded to each other.

15. The medical device of claim 14, wherein:
the dowel receptacle of the shaft proximal member includes at least one ridge to grip the shaft distal member and/or at least one recess to grip the shaft distal member.

16. The medical device of claim 1, wherein:
the dowel receptacle of the shaft proximal member is provided by a lumen of the shaft proximal member.

17. The medical device of claim 1, wherein:
the shaft proximal member and the shaft distal member have different colors.

18. The medical device of claim 1, wherein:
the dowel of the shaft distal member and the dowel receptacle of the shaft proximal member are friction fit to each other.

19. The medical device of claim 1, wherein:
the dowel of the shaft distal member and the dowel receptacle of the shaft proximal member are positively mechanically engaged to each other.

20. The medical device of claim 1, wherein:
the shaft proximal member and the shaft distal member are friction fit to each other.

21. The medical device of claim 1, wherein:
the shaft proximal member and the shaft distal member are positively mechanically engaged to each other.

22. The medical device of claim 1, wherein:
the single piece is a single injection molded piece.

23. The medical device of claim 1, wherein:
the introducer has a size of 6 French.

24. The medical device of claim 1, wherein:
the introducer has a size of 10 French.

25. The medical device of claim 1, wherein:
the introducer has a size of 15 French.

26. The medical device of claim 1, wherein:
the elastomer has a Shore A durometer hardness, as measured by ASTM D2240-15 (2021), in a range of 41-59 Shore A durometer hardness.

27. The medical device of claim 1, wherein:
the elastomer has a Shore A durometer hardness, as measured by ASTM D2240-15 (2021), in a range of 60-80 Shore A durometer hardness.

* * * * *